(12) United States Patent
Yamaki et al.

(10) Patent No.: US 11,433,157 B2
(45) Date of Patent: Sep. 6, 2022

(54) ABSORBENT ARTICLE

(71) Applicant: Unicharm Corporation, Ehime-Ken (JP)

(72) Inventors: Koichi Yamaki, Kanonji (JP); Takayoshi Konishi, Kanonji (JP); Hideaki Ichiura, Kochi (JP)

(73) Assignee: Unicharm Corporation, Ehime (JP)

( * ) Notice: Subject to any disclaimer, the term of this patent is extended or adjusted under 35 U.S.C. 154(b) by 711 days.

(21) Appl. No.: 16/446,020

(22) Filed: Jun. 19, 2019

(65) Prior Publication Data

US 2019/0298880 A1 Oct. 3, 2019

Related U.S. Application Data

(63) Continuation of application No. PCT/JP2017/046763, filed on Dec. 26, 2017.

(30) Foreign Application Priority Data

Dec. 28, 2016 (JP) .............................. JP2016-257058
Jul. 31, 2017 (JP) .............................. JP2017-148608

(51) Int. Cl.
*A61F 13/514* (2006.01)
*A61L 15/62* (2006.01)
(Continued)

(52) U.S. Cl.
CPC .............. *A61L 15/18* (2013.01); *A61F 13/15* (2013.01); *A61F 13/15252* (2013.01);
(Continued)

(58) Field of Classification Search
CPC ........ A61F 13/25252; A61F 2013/1526; A61F 2013/51433; A61F 2013/53481;
(Continued)

(56) References Cited

U.S. PATENT DOCUMENTS 3,840,512 A   10/1974  Brackman
4,944,734 A * 7/1990  Wallach ................ A61F 13/512
                                                    604/364
(Continued)

FOREIGN PATENT DOCUMENTS

JP    H06107401 A    4/1994
JP    H07502221 A    3/1995
(Continued)

OTHER PUBLICATIONS

International Search Report issued in corresponding application No. PCT/JP2017/046763 dated Mar. 27, 2018 (5 pages).

*Primary Examiner* — Catharine L Anderson
*Assistant Examiner* — Lynne Anderson
(74) *Attorney, Agent, or Firm* — Osha Bergman Watanabe & Burton LLP

(57) ABSTRACT

An absorbent article may include a top sheet that is liquid-permeable, a back sheet that is liquid-impermeable, and an absorbent body situated between the top sheet and the back sheet in a thickness direction. At least one of the top sheet and the back sheet may include a synthetic resin sheet that includes a synthetic resin component and an oxidative decomposer comprising a mixture of a carboxylate and a rare earth compound. The synthetic resin sheet may contain the oxidative decomposer in a mass ratio such that a decomposition rate index ($D_i$), as determined by formula (1), is 7.8 or less:

$$D_i = B_r \times S_a \qquad (1)$$

where $B_r$ represents a mass ratio (g/g) of the oxidative decomposer with respect to the synthetic resin component, and $S_a$ represents a specific surface area ($cm^2/g$) of the synthetic resin sheet.

20 Claims, 4 Drawing Sheets

(51) Int. Cl.

| | | |
|---|---|---|
| *A61L 15/18* | (2006.01) | |
| *A61F 13/15* | (2006.01) | |
| *A61L 15/22* | (2006.01) | |
| *B32B 27/18* | (2006.01) | |
| *C08L 101/00* | (2006.01) | |
| *A61F 13/53* | (2006.01) | |
| *B01J 20/24* | (2006.01) | |
| *C08K 3/00* | (2018.01) | |
| *A61F 13/511* | (2006.01) | |
| *A61F 13/534* | (2006.01) | |
| *A61F 13/496* | (2006.01) | |

(52) U.S. Cl.
CPC .......... *A61F 13/511* (2013.01); *A61F 13/514* (2013.01); *A61F 13/53* (2013.01); *A61F 13/534* (2013.01); *A61L 15/22* (2013.01); *A61L 15/62* (2013.01); *B01J 20/24* (2013.01); *B32B 27/18* (2013.01); *C08K 3/00* (2013.01); *C08L 101/00* (2013.01); *A61F 13/496* (2013.01); *A61F 2013/1526* (2013.01); *A61F 2013/51433* (2013.01); *A61F 2013/53481* (2013.01)

(58) Field of Classification Search
CPC ........ A61F 2013/530313; A61F 2013/530321; A61L 15/18; A61L 15/22; A61L 15/62
See application file for complete search history.

(56) References Cited

U.S. PATENT DOCUMENTS

| | | |
|---|---|---|
| 5,308,906 A | 5/1994 | Taylor et al. |
| 5,565,503 A | 10/1996 | Garcia et al. |
| 5,854,304 A | 12/1998 | Garcia et al. |
| 6,887,496 B2 * | 5/2005 | Koenig .................. A61L 15/46 424/431 |
| 2001/0003797 A1 | 6/2001 | Guevara et al. |

FOREIGN PATENT DOCUMENTS

| | | |
|---|---|---|
| JP | 2001521969 A | 11/2001 |
| JP | 2002035037 A | 2/2002 |
| JP | 2006521415 A | 9/2006 |
| WO | 8809354 A1 | 12/1988 |
| WO | 9311941 A2 | 6/1993 |
| WO | 9923163 A1 | 5/1999 |
| WO | 2004083266 A1 | 9/2004 |

\* cited by examiner

ABSORBENT ARTICLE

TECHNICAL FIELD

The present invention generally relates to an absorbent article, such as a disposable diaper, sanitary napkin or incontinence pad, which has a biodegradable property.

BACKGROUND

Among industrial products such as textile products and sheet products, products composed of petroleum-based resins such as polyethylene and polystyrene generate poisonous gases when subjected to disposal treatment by incineration or landfill, or remain in the soil and increase the load on the environment, and therefore in recent years research is being conducted on biodegradable resin substitutes for petroleum-based resins.

Such biodegradable resin substitutes for petroleum-based resins are also being investigated for absorbent articles such as disposable diapers, sanitary napkins and incontinence pads, and for example, PTL 1 proposes a biodegradable sanitary product wherein a film, nonwoven fabric, an adhesive tape and a water absorbing material, as the main structural members of the sanitary product, are biodegradable and the water absorbing material is composed of galactomannan, boron ion and a trivalent or greater polyvalent metal ion other than boron ion. The sanitary product disclosed in PTL 1 has excellent water absorption performance and an excellent feel, while also having excellent biodegradability in soil and compost.

Patent Literature 1: Japanese Unexamined Patent Publication No. 2002-35037

In the sanitary product (absorbent article) disclosed in Patent Literature 1, the resins used to form the nonwoven fabric (top sheet), the film (back sheet) and the adhesive tape are hydrolyzable biodegradable resins such as polylactic acid polymers, but such hydrolyzable biodegradable resins generally have lower molding workability than the aforementioned petroleum-based resins (synthetic resins) and are easily converted to low molecular weight compounds by hydrolysis. Therefore, absorbent articles that include structural members such as top sheets or back sheets that have been formed using such hydrolyzable biodegradable resins are inferior to those using conventional synthetic resins, in terms of the properties necessary for an absorbent article, including strength and durability. Decomposition of such resins may proceed whether the absorbent article is unused or in a state of being used, thus further impairing the properties, and hindering the use of the absorbent articles.

Various modifications have been tried to compensate for the drawbacks of hydrolyzable biodegradable resins, such as mixing general purpose synthetic resins with the hydrolyzable biodegradable resins, or mixing oxidative decomposers with general purpose synthetic resins to allow the molecular weight of the synthetic resins to be lowered to a biodegradable state. Employing such modifications, however, lowers the decomposition rate of the resins, and when the used absorbent articles are processed in a soil landfill, disintegration of the absorbent articles often becomes prolonged, increasing the environmental load at the landfill site.

SUMMARY

One or more embodiments provide an absorbent article that can maintain the same properties as an absorbent article using structural members composed of conventional synthetic resins, whether unused or while being used, and that after being disposed of and processed in a landfill after use, disintegrates within a short time period, thus reducing the environmental load at the landfill site.

An absorbent article according to one or more embodiments includes a liquid-permeable top sheet, a liquid-impermeable back sheet and an absorbent body situated between these sheets, with either or both the top sheet and the back sheet being formed of a synthetic resin sheet that includes an oxidative decomposer. The oxidative decomposer is made of a mixture of a carboxylate and a rare earth compound. The synthetic resin sheet includes an oxidative decomposer in a mass ratio such that a decomposition rate index ($D_i$) determined based on a following formula (1) is 7.8 or less. The absorbent article includes an oxidative decomposition accelerator composed of a peroxide, further toward a non-skin side than the absorbent body and/or inside water-sensitive capsules in the absorbent body, in a mass ratio of 40 parts by mass or greater with respect to 100 parts by mass of the oxidative decomposer.

$$D_i = B_r \times S_a \tag{1}$$

[In formula (1), $B_r$ represents a mass ratio (g/g) of the oxidative decomposer with respect to a synthetic resin component in the synthetic resin sheet, and $S_a$ represents a specific surface area (cm$^2$/g) of the synthetic resin sheet.]

Since the synthetic resin sheet forming either or both the top sheet and the back sheet in the absorbent article according to one or more embodiments includes an oxidative decomposer composed of a mixture of a carboxylate and a rare earth compound, in a specified mass ratio, then even if oxidative decomposition of the synthetic resin sheet by the oxidative decomposer has proceeded before the accelerating function of the oxidative decomposition accelerator is activated (that is, while the absorbent article is unused or in the state of being used), it proceeds gently, allowing the quality (structure and function) of the absorbent article to be maintained for at least 3 years. In addition, since the absorbent article according to one or more embodiments includes an oxidative decomposition accelerator composed of a peroxide in a specified mass ratio, further toward the non-skin side than the absorbent body and/or inside the water-sensitive capsules in the absorbent body, the oxidative decomposition accelerator is unlikely to contact with moisture such as excreted fluid (that is, the oxidative decomposition accelerator is unlikely to reach the oxidative decomposer in the synthetic resin sheet with the moisture such as excreted fluid as the mobile medium) while the absorbent article is unused or in the state of being used, making it possible to inhibit activation of the accelerating function of the oxidative decomposition accelerator, while even after the absorbent article has been disposed of and processed in a landfill after use, the oxidative decomposition accelerator can reach the oxidative decomposer in the synthetic resin sheet, with moisture in the soil as the mobile medium, and oxidative decomposition of the synthetic resin sheet by the oxidative decomposer can be accelerated, allowing the absorbent article to be disintegrated within a short time period.

Therefore, the absorbent article according to one or more embodiments can maintain the same properties as an absorbent article using structural members composed of conventional synthetic resins, whether unused or while being used, and after being disposed of and processed in a landfill after use, it can disintegrate within a short time period, thus reducing the environmental load at the landfill site.

In an absorbent article according to one or more embodiments, the oxidative decomposition accelerator is sodium percarbonate or hydrogen peroxide.

Since the oxidative decomposition accelerator according to one or more embodiments is sodium percarbonate or hydrogen peroxide, the above function and effect of the absorbent article can be more precisely and more reliably exhibited.

In an absorbent article according to one or more embodiments, the synthetic resin sheet includes the oxidative decomposer in a mass ratio such that the decomposition rate index ($D_i$) is 3.0 or greater.

Since the absorbent article according to one or more embodiments includes the oxidative decomposer in a specified mass ratio so that the decomposition rate index ($D_i$) is 3.0 or greater (that is, a mass ratio in the range of 3.0 to 7.8), then even if oxidative decomposition of the synthetic resin sheet by the oxidative decomposer is accelerated before the accelerating function of the oxidative decomposition accelerator is activated, it is possible to maintain the quality of the absorbent article for a longer period of time (specifically, for longer than about 55.5 months (about 4 years and 8 months) in an environment at 24° C.), while oxidative decomposition of the synthetic resin sheet by the oxidative decomposition accelerator can be accelerated after the absorbent article has been disposed of and processed in a landfill after use, allowing the absorbent article to be disintegrated within about 2 years, and the environmental load at the landfill site can be even more reliably alleviated.

In an absorbent article according to one or more embodiments, the absorbent article includes an oxidative decomposition accelerator further toward the non-skin side than the back sheet.

Since the absorbent article according to one or more embodiments includes the oxidative decomposition accelerator further toward the non-skin side than the liquid-impermeable back sheet, the oxidative decomposition accelerator is even less likely to contact with excreted fluid such as urine discharged by the wearer during use of the absorbent article (that is, the oxidative decomposition accelerator is even less likely to reach the oxidative decomposer in the synthetic resin sheet with the excreted fluid as the mobile medium), and activation of the accelerating function of the oxidative decomposition accelerator during use of the absorbent article can be more reliably inhibited. Thus, the absorbent article according to one or more embodiments can more precisely exhibit the aforementioned function and effect of the absorbent articles.

In an absorbent article according to one or more embodiments, the back sheet is non-air permeable.

Since the liquid-impermeable back sheet of the absorbent article according to one or more embodiments is non-air permeable, humidity produced from excreted fluid such as urine that has been absorbed in the absorbent body is less likely to reach the oxidative decomposition accelerator situated on the non-skin side of the back sheet (that is, the oxidative decomposition accelerator is unlikely to reach the oxidative decomposer in the synthetic resin sheet with moisture from humidity as the mobile medium), and activation of the accelerating function of the oxidative decomposition accelerator during use of the absorbent article can be even more reliably inhibited. Thus, the absorbent article according to one or more embodiments can even more reliably exhibit the aforementioned function and effect of the absorbent articles.

In one or more embodiments, the absorbent article includes an oxidative decomposition accelerator between the absorbent body and the back sheet.

Since the absorbent article according to one or more embodiments includes the oxidative decomposition accelerator between the absorbent body and the back sheet, excreted fluid such as urine discharged by the wearer during use of the absorbent article is unlikely to be absorbed in the absorbent body and thereby reach the oxidative decomposition accelerator situated on the non-skin side, (that is, the oxidative decomposition accelerator is unlikely to reach the oxidative decomposer in the synthetic resin sheet with excreted fluid as the mobile medium), and activation of the accelerating function of the oxidative decomposition accelerator during use of the absorbent article can be inhibited, while the oxidative decomposition accelerator can be deployed without using water-sensitive capsules. Furthermore, even after the absorbent article has been disposed of and processed in a landfill after use, the oxidative decomposition accelerator located at approximately the center in the thickness direction of the absorbent article readily spreads out across the entire absorbent article, with the mobile medium being moisture in the soil or excreted fluid such as urine that has seeped out from the absorbent body, and therefore oxidative decomposition of the synthetic resin sheet by the oxidative decomposer can be even more efficiently and reliably accelerated by the oxidative decomposition accelerator.

In an absorbent article according to one or more embodiments, the absorbent body includes superabsorbent polymer particles and the water-sensitive capsules containing the oxidative decomposition accelerator inside them, and the water-sensitive capsules are in contact with the superabsorbent polymer particles in the absorbent body.

Since the absorbent body of the absorbent article according to one or more embodiments includes superabsorbent polymer particles and water-sensitive capsules containing the oxidative decomposition accelerator inside them, and the water-sensitive capsules are in contact with the superabsorbent polymer particles in the absorbent body, then even when excreted fluid such as urine discharged by the wearer during use of the absorbent article has reached the absorbent body, the excreted fluid is absorbed into the superabsorbent polymer particles and is unlikely to reach the oxidative decomposition accelerator inside the water-sensitive capsules (that is, the oxidative decomposition accelerator is unlikely to reach the oxidative decomposer in the synthetic resin sheet with excreted fluid as the mobile medium), and it is possible to inhibit activation of the accelerating function of the oxidative decomposition accelerator during use of the absorbent article. Furthermore, even after the absorbent article has been disposed of and processed in a landfill after use, the water-sensitive capsules situated in approximately the center in the thickness direction of the absorbent article can dissolve or disintegrate by moisture in the soil or excreted fluid such as urine that seeps out from the superabsorbent polymer, thus releasing the oxidative decomposition accelerator inside them, and causing the oxidative decomposition accelerator to be spread out across the entire absorbent article, with the mobile medium being moisture in the soil or excreted fluid such as urine that has seeped out from the absorbent body, and therefore oxidative decomposition of the synthetic resin sheet by the oxidative decomposer can be even more efficiently and reliably accelerated by the oxidative decomposition accelerator.

In an absorbent article according to one or more embodiments, the absorbent body is composed of a first layer situated on the skin side and comprising a plurality of the superabsorbent polymer particles, and a second layer adjacent to the non-skin side of the first layer and comprising a plurality of the water-sensitive capsules.

Since the absorbent body of the absorbent article according to one or more embodiments is composed of a first layer situated on a skin side and comprising a plurality of the superabsorbent polymer particles, and a second layer adjacent to the non-skin side of the first layer and comprising a plurality of the water-sensitive capsules, then even when excreted fluid such as urine discharged by the wearer during use of the absorbent article reaches the absorbent body, the excreted fluid is absorbed by the superabsorbent polymer particles of the first layer situated on the skin side of the absorbent body, and is even less likely to reach the oxidative decomposition accelerator in the water-sensitive capsules of the second layer that is adjacent to the non-skin side of the first layer (that is, the oxidative decomposition accelerator is even less likely to reach the oxidative decomposer in the synthetic resin sheet with excreted fluid as the mobile medium), and therefore activation of the accelerating function of the oxidative decomposition accelerator during use of the absorbent article can be even more reliably inhibited. Thus, the absorbent article according to one or more embodiments can more reliably exhibit the aforementioned function and effect of the absorbent articles.

An absorbent article according to one or more embodiments includes a top sheet that is liquid-permeable; a back sheet that is liquid-impermeable; and an absorbent body situated between the top sheet and the back sheet in a thickness direction of the absorbent article. At least one of the top sheet and the back sheet comprises a synthetic resin sheet that includes a synthetic resin component and an oxidative decomposer. The oxidative decomposer comprises a mixture of a carboxylate and a rare earth compound. The synthetic resin sheet includes the oxidative decomposer in a mass ratio such that a decomposition rate index (Di) is 7.8 or less, as determined by the following formula (1):

$$D_i = B_r \times S_a \qquad (1)$$

where $B_r$ represents a mass ratio (g/g) of the oxidative decomposer with respect to the synthetic resin component, and $S_a$ represents a specific surface area ($cm^2/g$) of the synthetic resin sheet. The absorbent article includes an oxidative decomposition accelerator in a mass ratio of 40 parts by mass or greater with respect to 100 parts by mass of the oxidative decomposer. The oxidative decomposition accelerator is a peroxide. The oxidative decomposition accelerator is one or more of: situated further toward a back sheet side in the thickness direction than the absorbent body, and contained within water-sensitive capsules that are situated within the absorbent body.

According to an absorbent article of one or more embodiments, it is possible to maintain the same properties as an absorbent article using structural members composed of conventional synthetic resins, whether unused or in a state of being used, and after being disposed of and processed in a landfill after use, the article can disintegrate within a short time period, thus reducing the environmental load at the landfill site.

DETAILED DESCRIPTION

Embodiments of the present invention will now be explained in greater detail with reference to the accompanying drawings. In one or more embodiments, unless otherwise specified, the concept of "viewing an object (for example, an absorbent article or absorbent body) on the horizontal plane in the expanded state in the thickness direction of the object, from the upper side in the vertical direction", will be referred to simply by the phrase "in the plan view".

The directions used throughout the present specification are as follows, unless otherwise specified.

Throughout the present specification, the "lengthwise direction" is the "long direction of the lengths of a longitudinal object (for example, an absorbent article) in the plan view", the "widthwise direction" is the "short direction of the lengths of a longitudinal object in the plan view (short direction)", the "thickness direction" is the "vertical direction with respect to an object placed on the horizontal plane in the expanded state", with the lengthwise direction, widthwise direction and thickness direction being in a mutually perpendicular relationship. Also, throughout the present specification, the concept of the "relatively proximal side with respect to the lengthwise center axis line located at the center in the lengthwise direction and extending in the widthwise direction, in the lengthwise direction of a longitudinal object" will be referred to as the "inner side in the lengthwise direction", and the concept of the "relatively distal side with respect to the lengthwise center axis line, in the lengthwise direction of the longitudinal object" will be referred to as the "outer side in the lengthwise direction". Similarly, the "relatively proximal side with respect to the widthwise center axis line located at the center in the widthwise direction and extending in the lengthwise direction, in the widthwise direction of a longitudinal object" will be referred to as the "inner side in the widthwise direction", and the "relatively distal side with respect to the widthwise center axis line, in the widthwise direction of the longitudinal object", will be referred to as the "outer side in the widthwise direction".

Furthermore, in one or more embodiments, unless otherwise specified, the concept of the "relatively proximal side with respect to side of the wearer's skin when the absorbent article is worn" will be referred to as the "skin side", and the concept of the "relatively distal side with respect to the side of the wearer's skin when the absorbent article is worn" will be referred to as the "non-skin side", for the thickness direction of the absorbent article.

Figure 1:
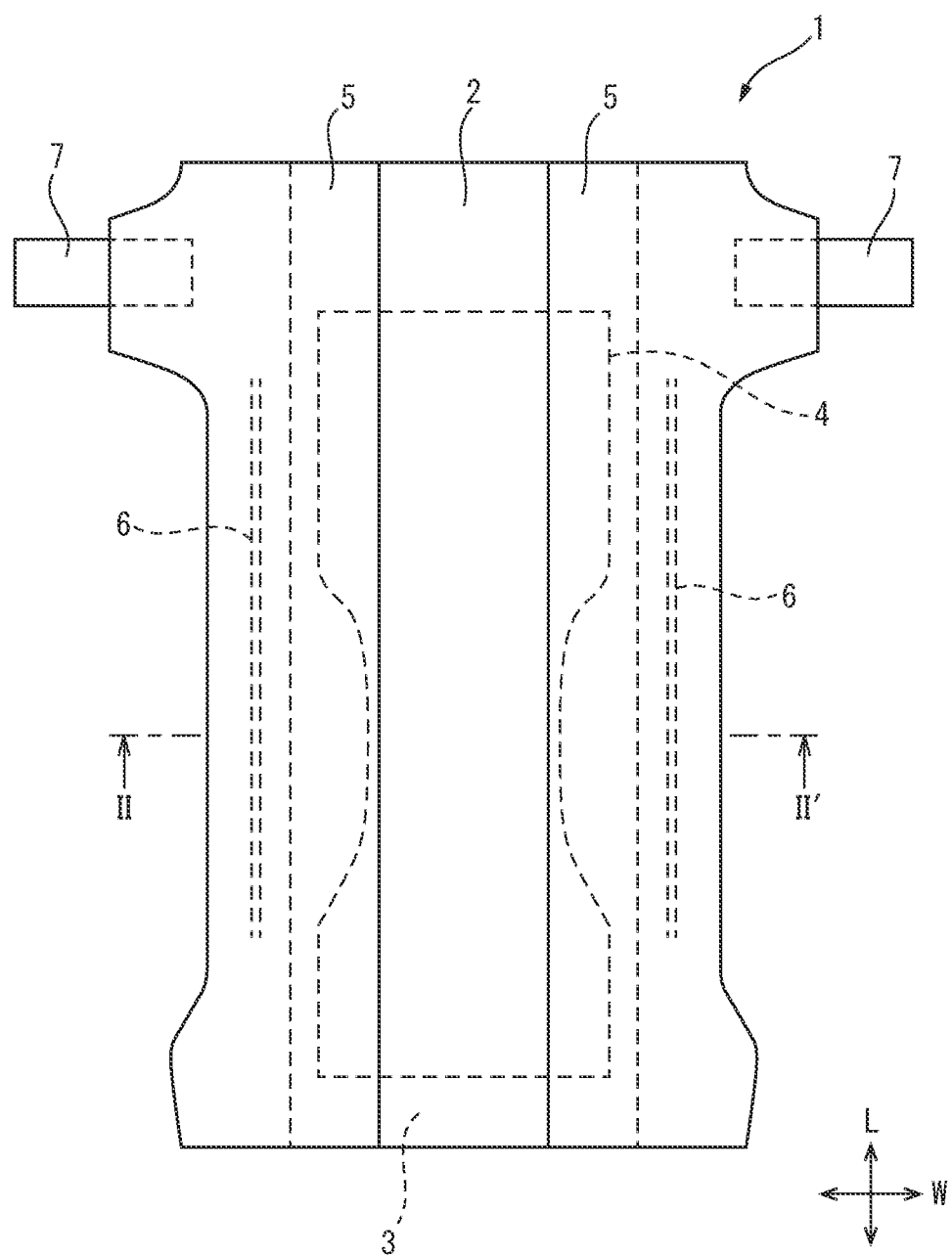
FIG. 1 is a plan view of a disposable diaper 1 according to one or more embodiments, as viewed in the thickness direction from the top sheet side, in the expanded state.
Figure 2:
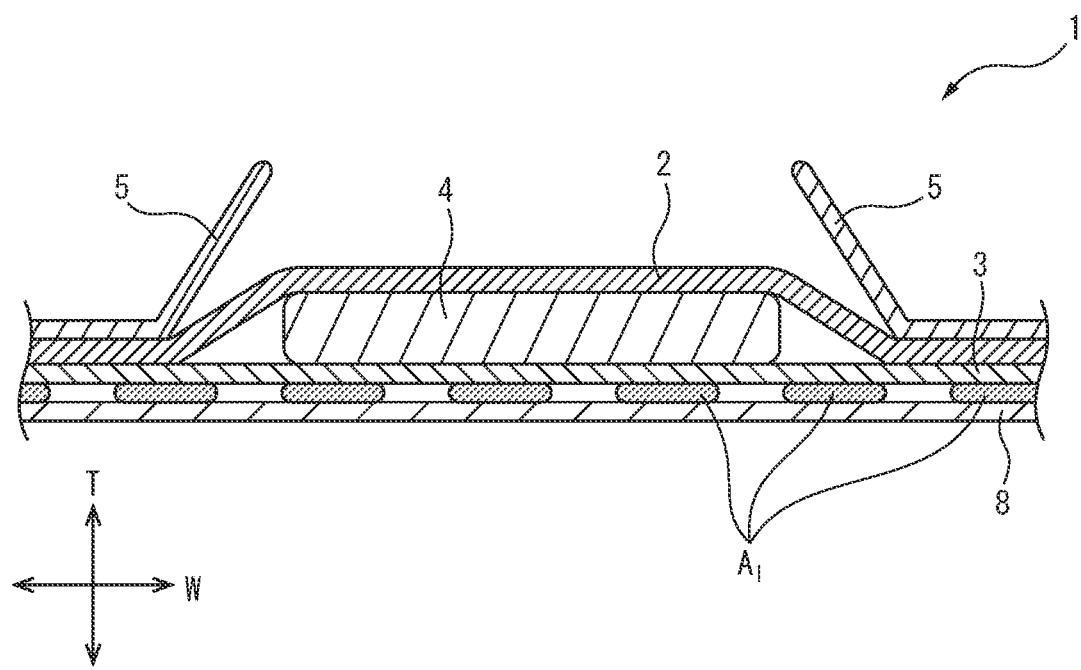
FIG. 2 is a partial cross-sectional end view of the disposable diaper 1 according to one or more embodiments, along line II-II' of FIG. 1.
Figure 3:
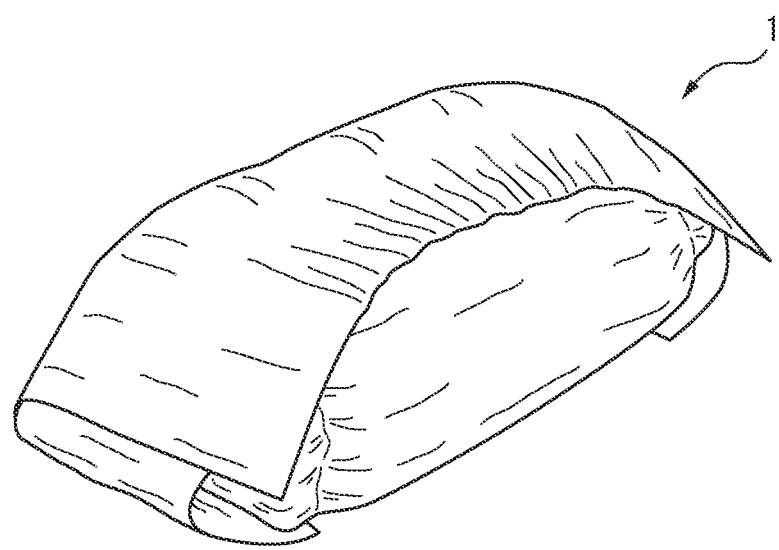
FIG. 3 is a perspective view showing the disposable diaper 1 when rolled up in the lengthwise direction after use for disposal.

FIG. 1 is a plan view of a disposable diaper 1 (absorbent article) having a biodegradable property according to one or more embodiments, as seen in the expanded state from the top sheet side in the thickness direction, and FIG. 2 is a partial cross-sectional end view of the disposable diaper 1 along line II-II' of FIG. 1. FIG. 3 is a perspective view showing the disposable diaper 1 when rolled up in the lengthwise direction after use for disposal.

As shown in FIG. 1 and FIG. 2, the disposable diaper 1 (absorbent article) according one or more embodiments has a lengthwise direction L, a widthwise direction W and a thickness direction T, which are mutually perpendicular, and in the plan view it has a longitudinal outer shape that is long in the lengthwise direction L. According to one or more embodiments, the outer shape of the absorbent article is not particularly restricted, and any desired outer shape such as essentially rectangular, essentially hourglass-shaped or ellipsoid, may be employed according to the purpose of use and the design property.

As shown in FIG. 1 and FIG. 2, the disposable diaper 1 of one or more embodiments comprises, as its main structural members in the thickness direction T, a liquid-permeable top sheet 2 situated on the side facing the skin of the wearer, a liquid-impermeable back sheet 3 situated on the side not facing the skin of the wearer, an absorbent body 4 situated between these two sheets, a pair of side sheets 5, 5 disposed on the skin-facing side of the top sheet 2 and functioning as anti-leakage walls when the disposable diaper 1 is worn, and a liquid-impermeable outer sheet 8 joined to the non-skin side of the back sheet 3 via any desired adhesive $A_1$ such as a hot-melt adhesive. The skin side and the non-skin side may be referred to as a top sheet side and a back sheet side in the thickness direction T, respectively. In one or more embodiments, the disposable diaper 1 is a tape-type disposable diaper comprising a stretching member 6 made of rubber thread or the like, disposed near the edges of the pair of side sheets 5, 5 on the outer sides in the widthwise direction W and causing the sections around the left and right legs contacting with the femoral regions of the wearer to stretch in the lengthwise direction L, and connecting tape 7 made of a mechanical fastener or the like, which connects the abdominal-corresponding region and the dorsal-corresponding region of the disposable diaper 1 when the disposable diaper 1 is worn. In the disposable diaper 1 shown in FIG. 1, the region at one end in the lengthwise direction L located at the lower end of FIG. 1 is the abdominal-corresponding region that corresponds to the abdominal region of the wearer of the disposable diaper 1, and the region at the other end in the lengthwise direction L located at the upper end of FIG. 1 is the dorsal-corresponding region that corresponds to the dorsal region (gluteal region) of the wearer of the disposable diaper 1.

In one or more embodiments, the top sheet 2 and back sheet 3 of the disposable diaper 1 are each formed of a synthetic resin sheet including an oxidative decomposer comprising a mixture of a carboxylate and a rare earth compound, the synthetic resin sheet including the oxidative decomposer at a mass ratio such that the decomposition rate index ($D_i$) is 7.8 or less, as determined based on the following formula (1).

$$D_i = B_r \times S_a \qquad (1)$$

[In formula (1), $B_r$ represents a mass ratio (g/g) of the oxidative decomposer with respect to a synthetic resin component in the synthetic resin sheet, and $S_a$ represents a specific surface area (cm$^2$/g) of the synthetic resin sheet.]

The disposable diaper 1 of one or more embodiments also includes an oxidative decomposition accelerator composed of a peroxide further toward the non-skin side than the absorbent body 4 (specifically, in the adhesive $A_1$ located on the non-skin side of the back sheet 3), at a mass ratio of 40 parts by mass or greater with respect to 100 parts by mass of the oxidative decomposer.

Since each synthetic resin sheet forming the top sheet 2 and back sheet 3 in the disposable diaper 1 of one or more embodiments includes an oxidative decomposer composed of a mixture of a carboxylate and a rare earth compound, in a specified mass ratio, then even when oxidative decomposition of the synthetic resin sheet by the oxidative decomposer has proceeded before the accelerating function of the oxidative decomposition accelerator is activated (that is, while the disposable diaper 1 is unused or in the state of being used), it proceeds gently, allowing the quality (structure and function) of the disposable diaper to be maintained for at least 3 years. In addition, since the disposable diaper 1 of the first embodiment includes an oxidative decomposition accelerator composed of a peroxide in a specified mass ratio, further toward the non-skin side than the absorbent body, the oxidative decomposition accelerator is unlikely to contact with moisture such as excreted fluid (that is, the oxidative decomposition accelerator is unlikely to reach the oxidative decomposer in the synthetic resin sheet with moisture such as excreted fluid as the mobile medium) while the disposable diaper 1 is unused or in the state of being used, making it possible to inhibit activation of the accelerating function of the oxidative decomposition accelerator, while even after the disposable diaper 1 has been disposed of and processed in a landfill after use in a state rolled up in the lengthwise direction L as shown in FIG. 3, the oxidative decomposition accelerator can reach the oxidative decomposer in the synthetic resin sheet, with moisture in the soil as the mobile medium, and oxidative decomposition of the synthetic resin sheet by the oxidative decomposer can be accelerated, allowing the disposable diaper 1 to be disintegrated within a short time period.

Therefore, the disposable diaper 1 of one or more embodiments can maintain the same properties as a disposable diaper using structural members composed of conventional synthetic resins, whether unused or in a state of being used, and after being disposed of and processed in a landfill after use, it can disintegrate within a short time period, thus reducing the environmental load at the landfill site.

Each of the members forming the absorbent article of one or more embodiments will now be explained in detail using the disposable diaper 1 of one or more embodiments described above.

[Top Sheet]

As shown in FIG. 1 and FIG. 2, the top sheet 2 used in the disposable diaper 1 of one or more embodiments is formed of a liquid-permeable synthetic resin sheet having, in the plan view, an essentially rectangular outer shape extending in the lengthwise direction L and widthwise direction W of the disposable diaper 1 and longitudinal in the lengthwise direction L, and in the thickness direction T of the disposable diaper 1, being disposed at a location (i.e. a location on the skin side) where excreted fluid such as urine discharged from the wearer is initially received, and functioning so that excreted fluid such as urine that has been discharged from the wearer is caused to rapidly migrate toward the absorbent body 4.

According to one or more embodiments, as mentioned above, the top sheet 2 may have a long rectangular outer shape in the lengthwise direction L of the disposable diaper 1 in the plan view, but embodiments are not limited to such a shape, and the top sheet (synthetic resin sheet) may have any desired outer shape and size.

According to one or more embodiments, the liquid-permeable synthetic resin sheet used to form the top sheet may be any type of synthetic resin sheet, and for example, it may be a synthetic resin fiber sheet such as a nonwoven fabric, woven fabric or knitted fabric made of synthetic resin fibers, or a synthetic resin film molded from a synthetic resin material and formed with liquid-permeable holes, but a synthetic resin fiber sheet such as a nonwoven fabric made of synthetic resin fibers, is used from the viewpoint of liquid permeability, flexibility and feel on the skin. The type of nonwoven fabric is not particularly restricted so long as it has the prescribed liquid permeability, flexibility and feel on the skin, and any type of nonwoven fabric may be employed such as an air-through nonwoven fabric, spunbond nonwoven fabric, spunlace nonwoven fabric or SMS, according to the desired function and purpose of use.

When a synthetic resin fiber sheet such as a nonwoven fabric is used as the top sheet, the constituent fibers used are not particularly restricted and may be fibers in any of various forms, including common forms of fibers having substantially circular cross-sectional shapes, as well as composite fibers such as core-sheath composite fibers or side-by-side composite fibers; atypical cross-section fibers in which the cross-sectional shapes are flat, for example; or solid crimped fibers with latent crimping or developed crimping.

The synthetic resin sheet forming the top sheet 2 of one or more embodiments is formed by a resin composition containing at least a synthetic resin and an oxidative decomposer. The resin composition may also optionally contain an additive or filler in addition to the synthetic resin and oxidative decomposer. Such a sheet made of a synthetic resin containing an oxidative decomposer (that is, an oxidative decomposing biodegradable resin) differs from a sheet made of a hydrolyzable biodegradable resin such as polylactic acid, modified starch or an aliphatic polyester, and can maintain physical properties (the physical properties necessary for an absorbent article, such as strength and durability) similar to those of a sheet made of a conventional non-biodegradable synthetic resin.

In one or more embodiments, the synthetic resin component to be included in the synthetic resin sheet that may be used to form the top sheet or the back sheet described below of one or more embodiments is not particularly restricted so long as it can be used as a structural member for an absorbent article, and any synthetic resin may be used, examples of which include polyolefin-based resins such as polyethylene, polypropylene, polybutylene, ethylene-vinyl acetate copolymer, ethylene-ethyl acrylate copolymer, ethylene-acrylic acid copolymer and ionomer resins; polystyrene-based resins such as polystyrene; polyester-based resins such as polyethylene terephthalate and polybutylene terephthalate; and polyamide-based resins such as nylon, with any of these synthetic resins being used alone as single types of resins, or in combinations of two or more different resins. Among these synthetic resins, those containing 50 mass % or greater of a polyolefin-based resin or polyolefin-based resin composition may be used, from the viewpoint of strength and durability, and of oxidative decomposition of the synthetic resin sheet after the absorbent article has been used. In one or more embodiments, in the polyolefin-based resin, polyethylene or polypropylene may be used. Particularly when the synthetic resin sheet is a nonwoven fabric, the fibers composing the nonwoven fabric may be core-sheath composite fibers formed of polypropylene as the core and polyethylene as the sheath.

Throughout the present specification, a "polyolefin-based resin composition" is a mixture of two or more polyolefin-based resins, or a mixture of a polyolefin-based resin and another resin with the polyolefin-based resin at 50 mass % or greater.

The oxidative decomposer of one or more embodiments is a substance that can oxidatively decompose synthetic resins and cause low molecularization of the synthetic resins to an extent allowing their biodegradation by microbes in the soil, and known ones include the oxidative decomposers disclosed in U.S. Pat. Nos. 3,840,512, 5,308,906, 5,565,503, 5,854,304 and International Patent Publication No. WO88/09354, for example, and especially those including one or more compounds selected from the group consisting of metal carboxylates, hydroxycarboxylic acids, transition metal compounds, rare earth compounds and aromatic ketones; for the purpose of one or more embodiments, however, the oxidative decomposer used may be an oxidative decomposer comprising a mixture of a carboxylate and a rare earth compound, in order to more precisely control progressive oxidative decomposition of the synthetic resin sheet (specifically, to control progressive oxidative decomposition of the synthetic resin sheet so that even when oxidative decomposition of the synthetic resin sheet by the oxidative decomposer proceeds before the accelerating function of the oxidative decomposition accelerator is activated (that is, while the absorbent article is still unused or is in the state of being used), it proceeds gently, allowing the quality (structure and function) of the absorbent article to be maintained for at least 3 years, while even after the absorbent article has been disposed of and processed in a landfill after use, the absorbent article can be caused to disintegrate within a short time period once the oxidative decomposition accelerator has reached the oxidative decomposer in the synthetic resin sheet with moisture in the soil as the mobile medium and accelerated oxidative decomposition of the synthetic resin sheet). An example of such an oxidative decomposer, as a commercial product, is "P-Life" (trade name) by P-Life Japan, Inc.

In one or more embodiments, the carboxylate to be used as an oxidative decomposer may be a metal salt of an aliphatic carboxylic acid of 10 to 20 carbon atoms. An example of the carboxylate to be used as an oxidative decomposer may be metal salts of stearic acid. Examples of metal atoms to form the metal salt of an aliphatic carboxylic acid include cobalt, cerium, iron, aluminum, antimony, barium, bismuth, chromium, copper, gallium, lanthanum, lithium, magnesium, molybdenum, nickel, calcium, silver, sodium, tin, tungsten, vanadium, yttrium, zinc and zirconium. In one or more embodiments, cobalt, cerium and iron may be used as metal atoms to form the metal salt of the aliphatic carboxylic acid. According to one or more embodiments, the carboxylate used may be a single carboxylate alone, or a combination of two or more carboxylates.

Examples of rare earth compounds to be used in the oxidative decomposer of one or more embodiments include rare earth elements such as cerium (Ce), yttrium (Y) and neodymium (Nd) belonging to Group 3 of the IUPAC Periodic Table, or their oxides, hydroxides, sulfates, nitrates, acetates, chlorides or carboxylates, and more specifically, they include cerium oxide, cerium (IV) sulfate, cerium (IV) ammonium sulfate, cerium (IV) ammonium nitrate, cerium acetate, lanthanum nitrate, cerium chloride, cerium nitrate, cerium hydroxide, cerium octylate, lanthanum oxide, yttrium oxide and scandium oxide. The rare earth compound used for one or more embodiments may be a single type of rare earth compound alone, or a combination of two or more different rare earth compounds.

In the disposable diaper 1 of one or more embodiments, the synthetic resin sheet includes the oxidative decomposer at a mass ratio such that the decomposition rate index ($D_i$) is no greater than 7.8, as determined based on the following formula (1).

$$D_i = B_r \times S_a \quad (1)$$

[In formula (1), $B_r$ represents the mass ratio (g/g) of the oxidative decomposer with respect to the synthetic resin component in the synthetic resin sheet, and $S_a$ represents the specific surface area ($cm^2/g$) of the synthetic resin sheet.]

The decomposition rate index $D_i$ here is an index of the decomposition rate, taking into account the quantitative elements of the oxidative decomposer and the structural elements of the synthetic resin sheet, and it is the index represented as the product of the mass ratio $B_r$ (g/g) of the oxidative decomposer with respect to the synthetic resin component in the synthetic resin sheet, and the specific surface area $S_a$ ($cm^2/g$) of the synthetic resin sheet. The specific surface area $S_a$ ($cm^2/g$) of the synthetic resin sheet used for calculation of the decomposition rate index $D_i$ is that represented as the surface area per unit mass of the synthetic resin sheet, and for the purpose of the present specification, it can be determined in the following manner according to the form of the synthetic resin sheet.

(i) When the synthetic resin sheet is a synthetic resin film having a thickness of about 10 μm to 50 μm, the specific surface area $S_a$ ($cm^2/g$) of the synthetic resin sheet can be obtained by multiplying the inverse of the mass per unit area (i.e. the basis weight) of the film by 2. For the specific surface area $S_a$ ($cm^2/g$) in this case, the area on both sides per unit mass of the film is the specific surface area $S_a$ ($cm^2/g$).

(ii) When the synthetic resin sheet is a synthetic resin fiber sheet (for example, a nonwoven fabric) comprising synthetic resin fibers having diameters of about 3 μm to 30 μm, the resin specific gravity and the size of the synthetic fibers are used to calculate the lateral area per unit mass of the synthetic fibers (the area of the sides (the cylindrical surfaces (peripheral surfaces)), assuming the shapes of the synthetic fibers to be circular columns), to obtain the specific surface area $S_a$ ($cm^2/g$) for the synthetic resin sheet.

As mentioned above, the synthetic resin sheet of one or more embodiments may include an oxidative decomposer composed of a mixture of a carboxylate and a rare earth compound, at a mass ratio such that the decomposition rate index ($D_i$) is no greater than 7.8. If the decomposition rate index ($D_i$) is in the range of no greater than 7.8, then the synthetic resin sheet can maintain its properties including structure and strength for at least about 3 years in an environment at 24° C. after the synthetic resin sheet has been produced, while the synthetic resin sheet can disintegrate by decomposition after a prescribed period of time as elapsed.

According to one or more embodiments, the upper limit of 7.8 for the decomposition rate index ($D_i$) was calculated as the value of the decomposition rate index ($D_i$) such that the disintegration time ($D_h$) is 216 hours or longer (that is, about 3 years or longer in an environment of 24° C.) in the heat acceleration test at 80° C., determined using a first order approximation determined from the relationship between the decomposition rate index ($D_i$) for multiple different synthetic resin sheets of previously known mixing proportion for the oxidative decomposer, and the disintegration time ($D_h$) based on a heat acceleration test at 80° C. measured using multiple synthetic resin sheets of the same type, as described below.

The heat acceleration test at 80° C. referred to here is a shortened test that allows prediction of the time required for a synthetic resin sheet to decompose to a point so that it no longer performs its function as a synthetic resin sheet (that is, disintegration of the synthetic resin sheet by decomposition) (i.e. the disintegration time ($D_h$)), wherein the synthetic resin sheet is placed in an environment (a 80° C. temperature environment) that is harsher than an actual environment (a 24° C. temperature environment) in which oxidative decomposition is promoted, so that oxidative decomposition of the synthetic resin sheet is accelerated, and the disintegration time ($D_h$) in the heat acceleration test at 80° C. can be measured in the following non-limiting manner. A disintegration time of 1 day (24 hours) in the heat acceleration test at 80° C. corresponds to 4 months in an environment of 24° C.

<Method of Measuring Disintegration Time ($D_h$) by Heat Acceleration Test at 80° C.>

(1) The synthetic resin sheet to be measured (a synthetic resin fiber sheet such as a nonwoven fabric, or a synthetic resin film) is cut to a prescribed size of 25 mm width, 200 mm length, to obtain a synthetic resin sheet measuring sample.

(2) One lengthwise edge of the obtained measuring sample (the top edge) is fixed with a jig, leaving the measuring sample in a hanging state, and a turn clip attached to a 10 g weight is affixed to the other lengthwise edge of the measuring sample (the lower edge), to obtain the measuring sample with a load applied.

(3) The measuring sample with the load applied is placed in an oven set to an internal temperature of 80° C., the timer is started, and the time (h) until the strength of the measuring sample falls below 0.1 N/25 mm and tearing occurs is measured. The measured time (h) is recorded as the disintegration time ($D_h$) for the synthetic resin sheet.

In one or more embodiments, different synthetic resin sheets (synthetic resin sheets of Production Examples 1 to 12) were produced in the following non-limiting manner, for use in determining the range of the decomposition rate index ($D_i$) giving the aforementioned mixing proportion of the oxidative decomposer.

A commercially available oxidative decomposer ("P-Life", trade name of P-Life Japan, Inc., SMC2360), 3 types of polyethylene resins (low-density polyethylene (LDPE): 2.3 mass %, linear low-density polyethylene (LLDPE): 83.90 mass %, high-density polyethylene (HDPE): 10 mass %), and a pigment (titanium oxide) were kneaded in an extruder in the mixing proportion shown in Table 1, and then an inflation method was used to produce a polyethylene film for Production Example 1 with a thickness of 25 μm.

Polyethylene films for Production Examples 2 to 4 were produced in the same manner as Production Example 1, except that the mixing proportion for the oxidative decomposer and the 3 types of polyethylene resins was changed to the mixing proportions listed in Table 1. Similarly, polyethylene films for Production Examples 5 to 8 were produced in the same manner as Production Example 1, except that the mixing proportion for the oxidative decomposer and the 3 types of polyethylene resins was changed to the mixing proportions listed in Table 1, and the film thickness was 37 μm.

In one or more embodiments, multiple types of nonwoven fabrics comprising polyolefin-based resin fibers were also produced in the following non-limiting manner, as different forms of synthetic resin sheets.

First, a polypropylene resin containing an added commercially available oxidative decomposer (trade name: "P-Life", by P-Life Japan, Inc., SMC2360), and a polyethylene resin containing the same added oxidative decomposer, were discharged through a spinning nozzle while melting them, to obtain composite synthetic fiber (size: 2.2 dtex, length: 51 mm) having a core-sheath structure with the polypropylene resin as the core and the polyethylene resin as the sheath. The mixing proportion of the oxidative decomposer with respect to the polypropylene resin and the mixing proportion of the oxidative decomposer with respect to the polyethylene resin were the same. After laminating the obtained composite synthetic fibers at a basis weight of 25 g/m², the laminate was bonded by hot air to produce an air-through nonwoven fabric for Production Example 9.

Air-through nonwoven fabrics for Production Examples 10 to 12 were produced in the same manner as Production Example 9, except that the mixing proportion for the oxidative decomposer was changed to the mixing proportions listed in Table 2.

The specific surface area and decomposition rate index ($D_i$) of each of the polyethylene films thus obtained in Production Examples 1 to 8 and each of the air-through nonwoven fabrics obtained in Production Examples 9 to 12 were calculated by the methods described above, and the disintegration time ($D_h$) of each synthetic resin sheet was measured according to <Method of measuring disintegration time ($D_h$) by heat acceleration test at 80° C.> above. The calculation results and measurement results are shown in Table 1 and Table 2. For the lateral area used for calculation of the specific surface area of the air-through nonwoven fabrics, the volume was determined from the mean specific gravity of the fibers, and the circular columnar lateral area was calculated assuming the fibers to be 10,000 m high circular columns.

TABLE 1

| | Construction | | Contents | | | | Decomposition | |
| | Basis weight | Specific surface area | Oxidative decomposer | Polyethylene resin | | | Pigment Titanium | rate index ($D_i$) | Disintegration time $D_h$ |
| | (g/m²) | (cm²/g) | SMC2360 | LDPE | LLDPE | HDPE | oxide | (cm²/g) | (h) |
|---|---|---|---|---|---|---|---|---|---|
| Prod. Ex. 1 | 23.5 | 851.1 | 0.25% | 2.3% | 83.90% | 10% | 3.60% | 2.13 | 333 |
| Prod. Ex. 2 | 23.5 | 851.1 | 0.50% | 4.5% | 81.40% | 10% | 3.60% | 4.26 | 286 |
| Prod. Ex. 3 | 23.5 | 851.1 | 0.75% | 6.8% | 78.90% | 10% | 3.60% | 6.38 | 257 |
| Prod. Ex. 4 | 23.5 | 851.1 | 1.00% | 9.0% | 76.40% | 10% | 3.60% | 8.51 | 210 |
| Prod. Ex. 5 | 35.0 | 571.4 | 0.25% | 2.3% | 83.90% | 10% | 3.60% | 1.43 | 390 |
| Prod. Ex. 6 | 35.0 | 571.4 | 0.50% | 4.5% | 81.40% | 10% | 3.60% | 2.86 | 360 |
| Prod. Ex. 7 | 35.0 | 571.4 | 0.75% | 6.8% | 78.90% | 10% | 3.60% | 4.29 | 310 |
| Prod. Ex. 8 | 35.0 | 571.4 | 1.00% | 9.0% | 76.40% | 10% | 3.60% | 5.71 | 325 |

TABLE 2

| | Construction | | | | Oxidative decomposer (SMC2360) content | Decomposition rate index ($D_i$) | Disintegration time $D_h$ |
| | Size (dtex) | Mean specific gravity | Side area (cm²) | Specific surface area (cm²/g) | | (cm²/g) | (h) |
|---|---|---|---|---|---|---|---|
| Prod. Ex. 9 | 2.2 | 0.95 | 5395 | 2452.1 | 0.10% | 2.45 | 260 |
| Prod. Ex. 10 | 2.2 | 0.95 | 5395 | 2452.1 | 0.20% | 4.90 | 240 |
| Prod. Ex. 11 | 2.2 | 0.95 | 5395 | 2452.1 | 0.30% | 7.36 | 228 |
| Prod. Ex. 12 | 2.2 | 0.95 | 5395 | 2452.1 | 0.50% | 12.26 | 68 |

Figure 4:
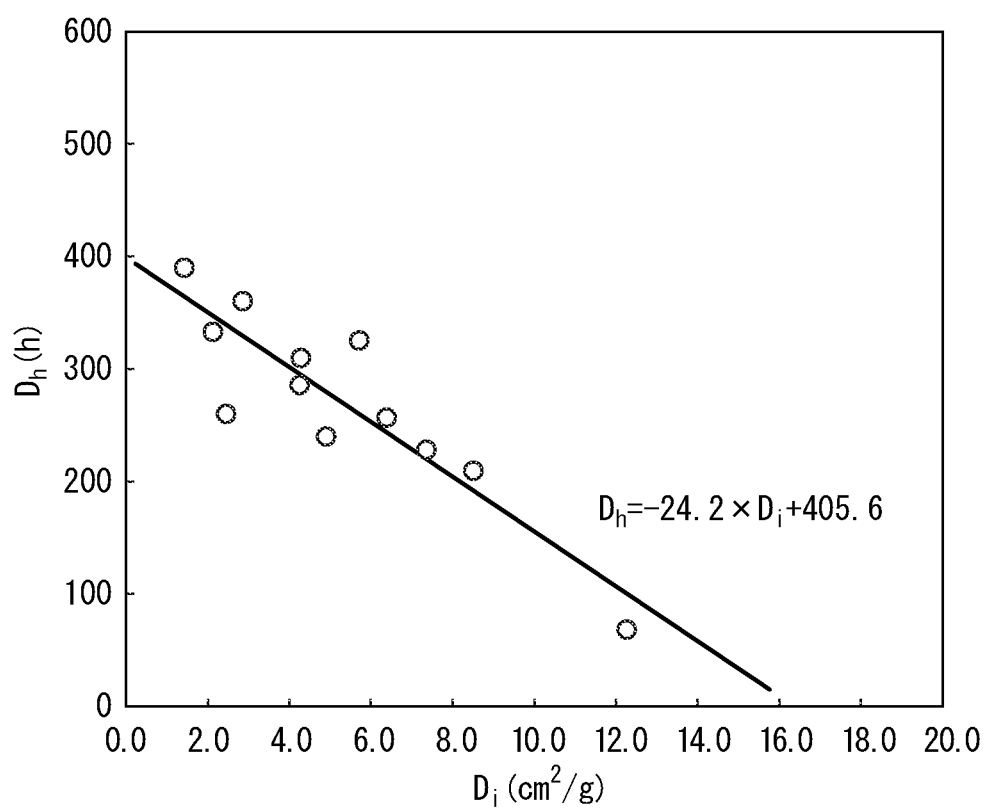
FIG. 4 is a graph showing the relationship between the decomposition rate index ($D_i$) of different synthetic resin sheets and the disintegration time $D_h$ in a heat acceleration test at 80° C.

FIG. 4 is a graph showing the relationship between the decomposition rate index ($D_i$) and the disintegration time ($D_h$) in a heat acceleration test at 80° C., for the polyethylene films (synthetic resin sheets) of Production Examples 1 to 8 and the air-through nonwoven fabrics (synthetic resin sheets) of Production Examples 9 to 12. As shown in the graph of FIG. 4, the decomposition rate index ($D_i$) and disintegration time $D_h$ in a heat acceleration test at 80° C. for each of the synthetic resin sheets obtained in the Production Examples are in a mutually proportional relationship, the first order approximation being $D_h=-24.2\times D_i+405.6$ (that is, k=−24.2). This first order approximation was used to calculate the value of the decomposition rate index ($D_i$) such that the disintegration time ($D_h$) was 216 hours (that is, about 3 years in an environment at 24° C.) in the heat acceleration test at 80° C., giving a value of 7.8.

According to one or more embodiments, incidentally, the disintegration time of a synthetic resin sheet may be adjusted in consideration of the warranty period of the product or environmental effects at the landfill site. In such cases, the disintegration time of the synthetic resin sheet can be more easily adjusted by appropriately modifying the mixing proportion of the oxidative decomposer according to the form (the type, structure and size) of the sheet and the type of synthetic resin.

The upper limit for the disintegration time of the synthetic resin sheet (that is, the lower limit for the decomposition rate index ($D_i$)) can be set as desired in consideration of the warranty period for use of the product and environmental effects at the landfill site, but from the viewpoint of the warranty period for use of the product (quality assurance period) before activation of the accelerating function of the oxidative decomposition accelerator, and the decomposition period after processing of the product of one or more embodiments at the landfill (after disposal), the disintegration time ($D_h$) in the heat acceleration test at 80° C. may be no longer than 333 hours (that is, it includes the oxidative decomposer in a mass ratio such that the decomposition rate index ($D_i$) is 3.0 or greater), and, in some embodiments, the disintegration time ($D_h$) in the heat acceleration test at 80° C. may be no longer than 266 hours (that is, it includes the oxidative decomposer in a mass ratio such that the decomposition rate index ($D_i$) is 5.8 or greater). For example, a disintegration time ($D_h$) of 266 hours in the heat acceleration test at 80° C. corresponds to about 44.3 months (about 3 years and 8 months) in an environment at 24° C., and when oxidative decomposition of the synthetic resin sheet is accelerated by the oxidative decomposition accelerator after the absorbent article has been disposed of and processed in a landfill after use, disintegration by oxidative decomposition can be shortened by about 20.3 months (that is, 122 hours of the heat acceleration test at 80° C.), thus allowing the absorbent article to be disintegrated within approximately 24 months (about 2 years), and allowing the environmental load at the landfill site to be more reliably alleviated.

The shortened period for the disintegration time of the synthetic resin sheet by the oxidative decomposition accelerator (for example, 122 hours in the heat acceleration test at 80° C.) can be determined by conducting a heat acceleration test at 80° C. using a synthetic resin sheet treated with the oxidative decomposition accelerator and a synthetic resin sheet not treated with the oxidative decomposition accelerator, and performing calculation from the relationship between the presence or absence of treatment with the oxidative decomposition accelerator and the disintegration time in the heat acceleration test at 80° C. For example, by subtracting the disintegration time in the heat acceleration test at 80° C. for the synthetic resin sheet of Example 1 that was subjected to oxidative decomposition acceleration treatment from the disintegration time in the heat acceleration test at 80° C. for the synthetic resin sheet of Comparative Example 1 that was not subjected to oxidative decomposition acceleration treatment, it is possible to calculate the shortened time (h) for the disintegration time of the synthetic resin sheet by the oxidative decomposition accelerator.

According to one or more embodiments, the top sheet does not necessarily need to be formed of a synthetic resin sheet including the amorphous oxidative decomposer, and for example, if the effect of one or more embodiments is adequately exhibited even when the back sheet is formed of a synthetic resin sheet that includes an oxidative decomposer and the top sheet is formed of a synthetic resin sheet that does not include the oxidative decomposer, then the top sheet may be formed of a synthetic resin sheet that does not include the oxidative decomposer.

The thickness and basis weight of the top sheet are not particularly limited so long as the effect of one or more embodiments is not inhibited, and any thickness and basis weight may be employed according to the desired liquid permeability and flexibility.

[Back Sheet]

As shown in FIG. 1 and FIG. 2, the back sheet 3 used in the disposable diaper 1 of one or more embodiments is formed of a liquid-impermeable synthetic resin sheet having, in the plan view, an essentially rectangular outer shape extending in the lengthwise direction L and widthwise direction W of the disposable diaper 1 and longitudinal in the lengthwise direction L, and in the thickness direction T of the disposable diaper 1, being disposed on the non-skin side of the absorbent body 4 and functioning to prevent permeation of excreted fluid such as urine that has been discharged by the wearer and to block outward leakage of the excreted fluid to the clothing of the wearer.

Incidentally, the back sheet 3 of one or more embodiments, while sandwiching the absorbent body 4 against the top sheet 2, is mutually joined with the top sheet 2 and the side sheets 5, 5. During joining, any joining means may be used such as, for example, bonding means by bonding with an adhesive such as a hot-melt adhesive or contact bonding means by various types of embossing treatment. According to one or more embodiments, the back sheet 3 has a long essentially rectangular outer shape in the lengthwise direction L of the disposable diaper 1 in the plan view, similar to the top sheet 2, but the embodiments are not limited to such a shape, and the back sheet (synthetic resin sheet) may have any desired outer shape and size.

According to one or more embodiments, the liquid-impermeable synthetic resin sheet used to form the back sheet may be a synthetic resin sheet similar to the top sheet described above, except for its liquid impermeability, and for example, any synthetic resin sheet may be used, including a synthetic resin fiber sheet such as a nonwoven fabric made of synthetic resin fibers that have been waterproof treated or that have hydrophobicity, or a non-porous synthetic resin film molded from a synthetic resin material. For one or more embodiments, the synthetic resin sheet forming the back sheet 3 is formed of a resin composition containing at least a synthetic resin and an oxidative decomposer, similar to the top sheet 2 described above, and since it is the same as the synthetic resin sheet forming the top sheet 2 in terms of the type of synthetic resin, the type of oxidative decomposer, and the mixing proportions (composition), structure and function, it will not be explained in detail.

According to one or more embodiments, the liquid-impermeable synthetic resin sheet forming the back sheet may have a constant air permeability or it may lack air permeability (that is, it may be non-air permeable), so long as it does not allow permeation of liquids such as excreted fluid (that is, so long as it has the prescribed liquid impermeability). When the oxidative decomposition accelerator is disposed further toward the non-skin side than the back sheet, the back sheet may be non-air permeable. If the liquid-impermeable back sheet is non-air permeable, humidity produced from excreted fluid such as urine that has been absorbed in the absorbent body is less likely to reach the oxidative decomposition accelerator situated on the non-skin side of the back sheet (that is, the oxidative decomposition accelerator is unlikely to reach the oxidative decomposer in the synthetic resin sheet with moisture from humidity as the mobile medium), and activation of the accelerating function of the oxidative decomposition accelerator during use of the absorbent article can be even more reliably inhibited. As used herein, "non-air permeable" refers to a water vapor permeability of no greater than 50 $g/m^2/24$ h according to JIS:K7129.

According to one or more embodiments, the back sheet does not necessarily need to be formed of a synthetic resin sheet including the amorphous oxidative decomposer, and for example, if the effect of one or more embodiments is adequately exhibited even when the top sheet is formed of a synthetic resin sheet that includes an oxidative decomposer and the back sheet is formed of a synthetic resin sheet that does not include the oxidative decomposer, then the back sheet may be formed of a synthetic resin sheet that does not include the oxidative decomposer.

The thickness and basis weight of the back sheet are not particularly limited so long as the effect of one or more embodiments is not inhibited, and any thickness and basis weight may be employed, depending on the desired liquid impermeability and flexibility.

[Side Sheets]

As shown in FIG. 1 and FIG. 2, the pair of side sheets 5, 5 to be used in the disposable diaper 1 of one or more embodiments are each formed of a liquid-impermeable or water-repellent synthetic resin sheet having, in the plan view, a pair of strip-like outer shapes that are long in the lengthwise direction L and extend partially in the lengthwise direction L and widthwise direction W of the disposable diaper 1, and being disposed on the skin-facing side of the top sheet 2 at both ends in the widthwise direction W of the disposable diaper 1, functioning as anti-leakage walls to block excreted fluid such as urine that has been discharged by the wearer, from leaking in the widthwise direction W of the disposable diaper 1.

According to one or more embodiments, the pair of side sheets 5, 5 each have a strip-like outer shape that is long in the lengthwise direction L of the disposable diaper 1, but the embodiments are not limited to such a shape, and the side sheets (synthetic resin sheets) may have any desired outer shape and size.

According to one or more embodiments, the liquid-impermeable or water-repellent synthetic resin sheets used to form the side sheets may be synthetic resin sheets similar to the top sheet described above, except for their liquid impermeability or water-repellency, and any synthetic resin sheets may be used including, for example, synthetic resin fiber sheets such as nonwoven fabrics made of synthetic resin fibers that have been waterproof treated or water-repellent treated, or that have hydrophobicity or water-repellency, or non-porous synthetic resin films molded from synthetic resin materials. The synthetic resin sheets forming the side sheets may likewise be formed of a resin composition containing at least a synthetic resin and an oxidative decomposer, similar to the top sheet described above, and since this is the same as the synthetic resin sheet forming the top sheet in terms of the type of synthetic resin, the type of oxidative decomposer, and the mixing proportions (composition), structure and function, it will not be explained in detail.

The thickness and basis weight of the side sheets are not particularly limited so long as the effect of one or more embodiments is not inhibited, and any thickness and basis weight may be employed according to the desired leakproofness and flexibility. Since having such a pair of side sheets is not an essential constituent feature for the absorbent article of one or more embodiments, it may lack the pair of side sheets, depending on the type and intended use of the absorbent article.

[Absorbent Body]

As shown in FIG. 1 and FIG. 2, the absorbent body 4 used in the disposable diaper 1 of one or more embodiments is formed of an absorbing member having, in the plan view, an essentially hourglass-like outer shape extending in the lengthwise direction L and widthwise direction W of the disposable diaper 1 and longitudinal in the lengthwise direction L, and in the thickness direction T of the disposable diaper 1, disposed between the top sheet 2 and the back sheet 3 and functioning to absorb and hold excreted fluid such as urine that has permeated the top sheet 2. According to one or more embodiments, as mentioned above, the absorbent body 4 has an essentially hourglass-like outer shape in the plan view, but the embodiments are not limited to such a shape, and the absorbent body may have any desired outer shape (for example, essentially rectangular that is long in the lengthwise direction, or ellipsoid), and size.

According to one or more embodiments, the absorbing member forming the absorbent body is not particularly restricted so long as it can absorb and hold excreted fluid, and any absorbing member known in the field may be used. For example, the absorbing member may be constructed of an absorbent core made of an absorbent material containing water-absorbent fibers and a superabsorbent polymer, and at least one liquid-permeable core wrap sheet that covers the outer peripheral surface of the absorbent core.

The water-absorbent fibers composing the absorbent core are not particularly restricted so long as they can absorb and hold liquid such as excreted fluid, and examples include wood pulp obtained using conifer or broadleaf tree as starting material; nonwood pulp such as kenaf, bamboo, hemp and cotton; regenerated cellulose such as rayon and fibril rayon; and semi-synthetic cellulose such as acetate and triacetate, but in consideration of biodegradability and environmental effects at landfill sites when the absorbent article is processed in a landfill, plant-derived cellulosic fibers such as wood pulp or nonwood pulp may be used. Like the water-absorbent fibers, the superabsorbent polymer composing the absorbent core is not particularly restricted so long as it can absorb and hold liquid such as excreted fluid, and for example, a starch-based, cellulosic or synthetic polymer-based superabsorbent polymer may be used, but one that is biodegradable may be used in consideration of environmental effects at landfill sites. Since the water-absorbent fibers and superabsorbent polymer composing the absorbent core are not essential constituent elements for the absorbent core, the absorbent core may contain only either the water-absorbent fibers or superabsorbent polymer alone.

The core wrap sheet is not particularly restricted so long as it is liquid-permeable and can maintain the shape of the absorbent body, but it may be biodegradable in consideration of effect on the environment at the landfill site, and for example, a liquid-permeable sheet such as a tissue made of the aforementioned cellulosic fibers may be suitably used.

According one or more embodiments, described below, the absorbent body may include superabsorbent polymer particles and water-sensitive capsules containing the oxidative decomposition accelerator inside them. An absorbent body including water-sensitive capsules will be described below in detail as one or more other embodiments.

The thickness and basis weight of the absorbent body are not particularly limited so long as the effect of one or more embodiments is not inhibited, and any thickness and basis weight may be employed according to the desired absorption property and flexibility.

[Outer Sheet]

The outer sheet 8 used in the disposable diaper 1 of one or more embodiments is formed of a liquid-impermeable synthetic resin sheet having, in the plan view, an essentially rectangular outer shape extending in the lengthwise direction L and widthwise direction W so as to cover the entire surface on the non-skin side of the disposable diaper 1, and being longitudinal in the lengthwise direction L, and as shown in FIG. 2, in the thickness direction T of the disposable diaper 1, it is disposed on the non-skin side of the back sheet 3 via a desired adhesive $A_1$ such as a hot-melt adhesive, and functions to prevent leakage of excreted fluid such as urine that has been discharged by the wearer while defining the outer shape of the disposable diaper 1.

According to one or more embodiments, the liquid-impermeable synthetic resin sheet used to form the outer sheet may be a synthetic resin sheet similar to the back sheet described above (that is, a synthetic resin sheet similar to the top sheet described above, except for being liquid-impermeable), and any synthetic resin sheet may be used including, for example, a synthetic resin fiber sheet such as a nonwoven fabric made of synthetic resin fibers that have been waterproof treated or that have hydrophobicity (for example, a spunbond nonwoven fabric, SMS nonwoven fabric or point bond nonwoven fabric), or a non-porous synthetic resin film molded from a synthetic resin material. The outer sheet may be composed of a single synthetic resin sheet, or it may be composed of two or more synthetic resin sheets. The synthetic resin sheets forming the outer sheet may likewise be formed of a resin composition containing at least a synthetic resin and an oxidative decomposer, similar to the top sheet described above, and since this is the same as the synthetic resin sheet forming the top sheet in terms of the type of synthetic resin, the type of oxidative decomposer, and the mixing proportions (composition), structure and function, it will not be explained in detail.

The thickness and basis weight of the outer sheet are not particularly limited so long as the effect of one or more embodiments is not inhibited, and any thickness and basis weight may be employed according to the desired liquid impermeability and flexibility. Since having such an outer sheet is not an essential constituent feature for the absorbent article of one or more embodiments, it may lack the outer sheet, depending on the type and intended use of the absorbent article.

[Adhesive]

For one or more embodiments, the adhesive $A_1$ joining the back sheet 3 and the outer sheet 8 is not particularly restricted, and any adhesive that is known in the relevant field may be used. Examples of such adhesives include hot-melt adhesives such as styrene-isoprene-styrene block copolymer (SIS), styrene-butadiene-styrene block copolymer (SBS) and styrene-ethylene-butylene-ethylene copolymer (SEBS).

The coating amount and coating form of the adhesive of one or more embodiments are not particularly restricted so long as they do not inhibit the effect of one or more embodiments, and any coating amount (for example, 0.1 $g/m^2$ to 10 $g/m^2$) and coating form (for example, one or more straight lines, belt shapes, spiral shapes, omega shapes or zigzag shapes) may be employed.

For one or more embodiments, the adhesive $A_1$ joining the back sheet 3 and the outer sheet 8 includes an oxidative decomposition accelerator composed of a peroxide in a mass ratio of 40 parts by mass or greater with respect to 100 parts by mass of the oxidative decomposer. Since the disposable diaper 1 of one or more embodiments includes an oxidative decomposition accelerator composed of a peroxide in the specified mass ratio, in the adhesive $A_1$ that is situated further toward the non-skin side than the back sheet 3, the oxidative decomposition accelerator will be unlikely to contact with moisture such as excreted fluid (that is, the oxidative decomposition accelerator will be unlikely to reach the oxidative decomposer in the synthetic resin sheet forming the top sheet 2 or back sheet 3, with moisture such as excreted fluid as the mobile medium), whether the disposable diaper 1 is unused or in a state of being used, allowing activation of the accelerating function of the oxidative decomposition accelerator to be inhibited and allowing the oxidative decomposition accelerator to be provided without using the water-sensitive capsules. Furthermore, after the disposable diaper 1 has been disposed of and processed in a landfill, in a state rolled up in the lengthwise direction L, the oxidative decomposition accelerator can reach the oxidative decomposer in each synthetic resin sheet with moisture in the soil as the mobile medium, oxidative decomposition of each synthetic resin sheet can be accelerated by the oxidative decomposer, and the disposable diaper 1 can be disintegrated within a short time period.

According to one or more embodiments, the peroxide to be used as the oxidative decomposition accelerator is not particularly restricted so long as it can accelerate oxidative decomposition of the synthetic resin by the oxidative decomposer comprising the mixture of a carboxylate and a rare earth compound, and examples include inorganic peroxides such as sodium percarbonate (Sodium percarbonate, CAS No. 15630-89-4), lithium peroxide, barium peroxide, magnesium peroxide and calcium peroxide, and hydrogen peroxide, any of which compounds may be used as single compounds or as combinations of more than one compound. Among such compounds, sodium percarbonate or hydrogen peroxide may be used as the oxidative decomposition accelerator, from the viewpoint of allowing more precise and reliable action of oxidative decomposition of the synthetic resin by the oxidative decomposer. For oxidative decomposition accelerators composed of such peroxides, when the peroxide is hydrogen peroxide, the hydrogen peroxide supplies hydroxyl radicals (OH radicals) to the oxidative decomposer, and when the peroxide is a compound other than hydrogen peroxide, the hydrogen peroxide produced by dissolution in water supplies hydroxyl radicals to the oxidative decomposer, thus accelerating oxidative decomposition by the oxidative decomposer.

The oxidative decomposition accelerator to be used in the absorbent article of one or more embodiments is used in a mass ratio of 40 parts by mass or greater with respect to 100 parts by mass of the oxidative decomposer, in order to sufficiently accelerate oxidative decomposition of the synthetic resin by the oxidative decomposer composed of the mixture of a carboxylate and a rare earth compound.

According to one or more embodiments, the adhesive that joins the back sheet and outer sheet does not necessarily have to include the oxidative decomposition accelerator, and the oxidative decomposition accelerator may be included in locations other than that adhesive (for example, in the adhesive joining the absorbent body with a leakproof sheet disposed on the non-skin side of the absorbent body, as in a different embodiment described below (embodiment 2), or inside water-sensitive capsules in the absorbent body, as in yet another embodiment described below (embodiment 3)), and if the effect of one or more embodiments is adequately exhibited thereby, the adhesive joining the back sheet and the outer sheet does not need to include the oxidative decomposition accelerator.

One or more embodiments (second embodiment and third embodiment), that differ from those described above in the aspect of the placement of the oxidative decomposition accelerator, will now be described in detail with reference to the accompanying drawings. The aspects of the construction other than the parts differing from the aforementioned embodiments are basically the same as the construction for the aforementioned embodiments, and therefore they will not be explained here.

Second Embodiment

Figure 5:
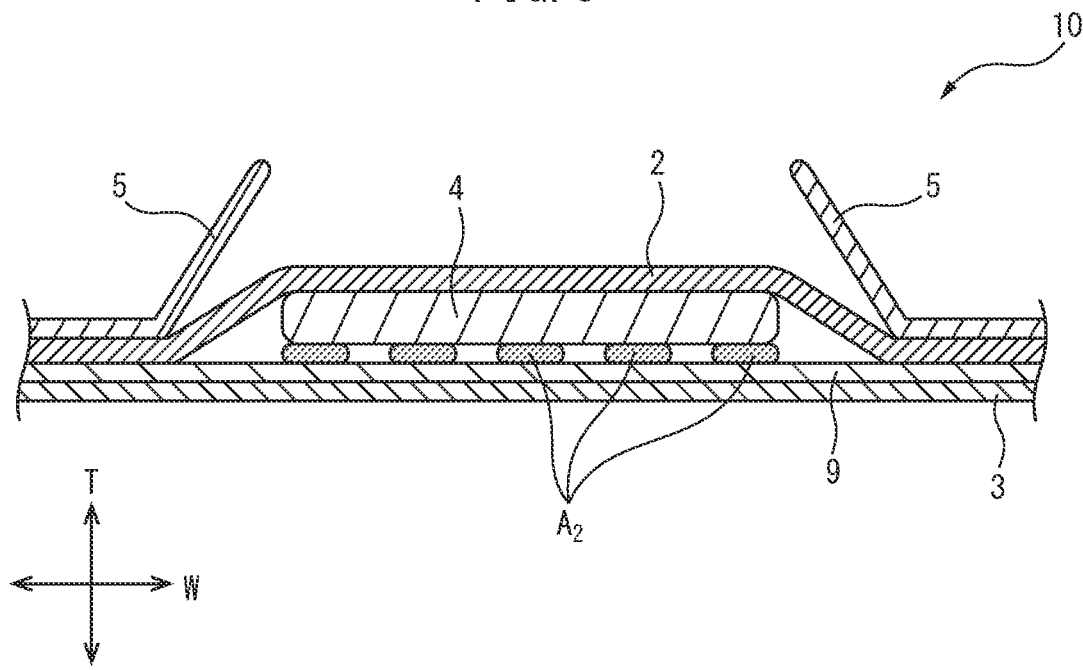
FIG. 5 is a partial end view corresponding to FIG. 2, of a disposable diaper 10 according to one or more embodiments.

FIG. 5 is a partial end view corresponding to FIG. 2, of a disposable diaper 10 according to one or more embodiments.

As shown in FIG. 5, the disposable diaper 10 (absorbent article) of one or more embodiments comprises, in the thickness direction T, a leakproof sheet 9 joined, as a structural member, to the non-skin side of the absorbent body 4 via any adhesive $A_2$ such as a hot-melt adhesive. The leakproof sheet 9 has, in the plan view, an essentially rectangular outer shape that is longitudinal in the lengthwise direction L, extending in the lengthwise direction L and the widthwise direction W so as to cover the entire surface on the non-skin side of the absorbent body 4, and it is formed on the non-skin side of the absorbent body 4 (more specifically, between the absorbent body 4 and the back sheet 3), by a liquid-impermeable synthetic resin sheet that prevents leakage of excreted fluid such as urine that has been discharged by the wearer and functions to block outward leakage of excreted fluid onto the clothing of the wearer, similar to the back sheet 3.

According to one or more embodiments, the liquid-impermeable synthetic resin sheet used to form the leakproof sheet may be a synthetic resin sheet similar to the back sheet described above (that is, a synthetic resin sheet similar to the top sheet described above, except for being liquid-impermeable), and any synthetic resin sheet may be used, such as a synthetic resin film molded from a synthetic resin material that has been leakproof treated or that has hydrophobicity. The synthetic resin sheet forming the leakproof sheet may likewise be formed of a resin composition containing at least a synthetic resin and an oxidative decomposer, similar to the top sheet described above, and since it is the same as the synthetic resin sheet forming the top sheet in terms of the type of synthetic resin, the type of oxidative decomposer, and the mixing proportions (composition), structure and function, it will not be explained in detail.

The thickness and basis weight of the leakproof sheet are not particularly limited so long as the effect of one or more embodiments is not inhibited, and any thickness and basis weight may be employed according to the desired liquid impermeability and flexibility. Since having such a leakproof sheet is not an essential constituent feature for the absorbent article of one or more embodiments, it may lack the leakproof sheet, depending on the type and intended use of the absorbent article.

For one or more embodiments, the adhesive $A_2$ in the disposable diaper 10 joining the absorbent body 4 and the leakproof sheet 9 includes the oxidative decomposition accelerator composed of a peroxide in the aforementioned specified mixing proportion (that is, in a mass ratio of 40 parts by mass or greater with respect to 100 parts by mass of the oxidative decomposer). Since the disposable diaper 10 of one or more embodiments includes the oxidative decomposition accelerator composed of a peroxide in the adhesive $A_2$ that is situated between the absorbent body 4 and the back sheet 3, then when the disposable diaper 10 is in a state of being used (especially when the amount of excreted fluid such as urine discharged by the wearer is minimal), excreted fluid such as urine discharged by the wearer is absorbed into the absorbent body 4, thus being unlikely to reach the oxidative decomposer located on the non-skin side (that is, the oxidative decomposition accelerator is unlikely to reach the oxidative decomposer in the synthetic resin sheet forming the top sheet 2 or back sheet 3, with excreted fluid as the mobile medium), making it possible to inhibit activation of the accelerating function of the oxidative decomposition accelerator during use of the disposable diaper 10, and allowing the oxidative decomposition accelerator to be provided without using water-sensitive capsules. Furthermore, even after the disposable diaper 10 has been disposed of and processed in a landfill after use, in a state rolled up in the lengthwise direction L, the oxidative decomposition accelerator located at approximately the center in the thickness direction T of the disposable diaper 10 readily spreads out across the entire disposable diaper 10, with the mobile medium being moisture in the soil or excreted fluid such as urine that has seeped out from the absorbent body 4, and therefore oxidative decomposition of each synthetic resin sheet by the oxidative decomposer can be even more efficiently and reliably accelerated by the oxidative decomposition accelerator.

Since this function and effect is exhibited by including the oxidative decomposition accelerator between the absorbent body and back sheet, the oxidative decomposition accelerator of one or more embodiments may also be included at any location other than the adhesive joining the absorbent body and leakproof sheet (for example, on the surface on the non-skin side of the leakproof sheet).

Moreover, the type of adhesive joining the absorbent body and leakproof sheet, as well as its coating coverage and manner of coating, are not particularly restricted according to one or more embodiments so long as the effect of one or more embodiments is not inhibited, and the same may be employed as for the adhesive joining the back sheet and outer sheet for one or more embodiments described above.

Incidentally, while one or more embodiments do not have an outer sheet on the non-skin side of the back sheet 3, there is no limitation to this aspect for the embodiments, and the absorbent article may also have an outer sheet joined with an adhesive on the non-skin side of the back sheet, as described above.

Figure 6:
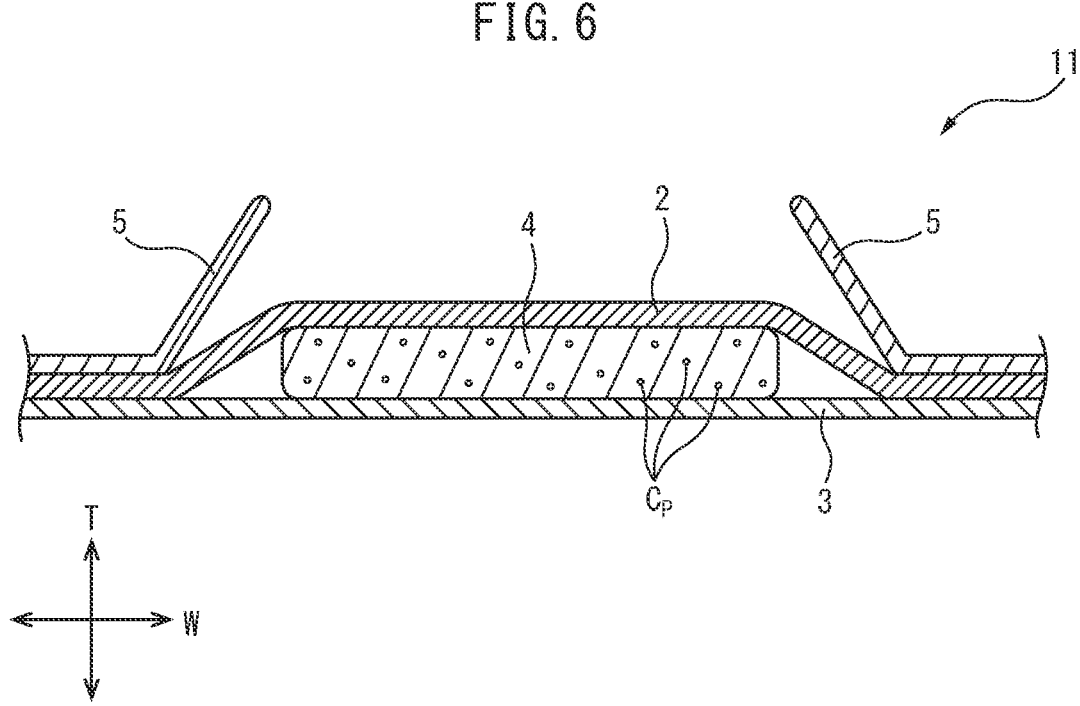
FIG. 6 is a partial end view corresponding to FIG. 2, of a disposable diaper 11 according to one or more embodiments.

FIG. 6 is a partial end view corresponding to FIG. 2, of a disposable diaper 11 according to one or more embodiments.

As shown in FIG. 6, the absorbent body 4 of the disposable diaper 11 of one or more embodiments includes super-absorbent polymer particles and a plurality of water-sensitive capsules $C_P$ containing the aforementioned oxidative decomposition accelerator composed of a peroxide inside them, the plurality of water-sensitive capsules $C_P$ containing the oxidative decomposition accelerator composed of a peroxide in a mass ratio of 40 parts by mass or greater with respect to 100 parts by mass of the oxidative decomposer, for the plurality of the water-sensitive capsules $C_P$ as a whole. Since the disposable diaper 11 of one or more embodiments includes the oxidative decomposition accelerator composed of a peroxide in the specified mass ratio inside the water-sensitive capsules in the absorbent body 4, then even whether the disposable diaper 11 is unused or in the state of being used, the oxidative decomposition accelerator is unlikely to contact with moisture such as excreted fluid (that is, the oxidative decomposition accelerator is unlikely to reach the oxidative decomposer in the synthetic resin sheet forming the top sheet 2 or back sheet 3, with moisture such as excreted fluid as the mobile medium), and activation of the accelerating function of the oxidative decomposition accelerator can be inhibited. Furthermore, after the disposable diaper 11 has been disposed of and processed in a landfill, in a state rolled up in the lengthwise direction L, the outer shells of the water-sensitive capsules $C_P$ dissolve or disintegrate releasing the oxidative decomposition accelerator inside them, and the oxidative decomposition accelerator can thus reach the oxidative decomposer in each synthetic resin sheet with moisture in the soil as the mobile medium, oxidative decomposition of each synthetic resin sheet can be accelerated by the oxidative decomposer, and the disposable diaper 1 can be disintegrated within a short time period.

As used herein, "water sensitivity" means the property of gradually dissolving or disintegrating upon contact with water, which is a property including water solubility and water disintegratability. It therefore means that the water-sensitive capsules are capsules whose outer shells gradually dissolve or disintegrate upon contact with water (that is, after elapse of a prescribed dissolution time or disintegration time).

According to one or more embodiments, the material forming the outer shells of the water-sensitive capsules is not particularly restricted so long as the effect of one or more embodiments is not inhibited, and examples are compounds such as polyethylene glycol or dextrin. The means for forming the water-sensitive capsules encapsulating the peroxide is also not particularly restricted so long as the effect of one or more embodiments is not inhibited, and it may be surface-coating means such as modification of the surfaces of the peroxide particles after the material forming the outer shells of the capsules has been dispersed on the surfaces, such as disclosed in Japanese Unexamined Patent Publication HEI No. 6-107401, for example.

According to one or more embodiments, the manner in which the water-sensitive capsules are disposed in the absorbent body is not particularly restricted. In one or more embodiments, the water-sensitive capsules are disposed so as to be in contact with the superabsorbent polymer particles in the absorbent body. If the water-sensitive capsules are in contact with the superabsorbent polymer particles in the absorbent body, then even when excreted fluid such as urine discharged by the wearer during use of the absorbent article has reached the absorbent body, the excreted fluid will be absorbed into the superabsorbent polymer particles and will be unlikely to reach the oxidative decomposition accelerator inside the water-sensitive capsules (that is, the oxidative decomposition accelerator will be unlikely to reach the oxidative decomposer in the synthetic resin sheet forming the top sheet or back sheet, with excreted fluid as the mobile medium), and it will therefore be possible to inhibit activation of the accelerating function of the oxidative decomposition accelerator during use of the absorbent article. Furthermore, even after the absorbent article has been disposed of and processed in a landfill after use, the water-sensitive capsules situated in approximately the center in the thickness direction of the absorbent article can dissolve or disintegrate by moisture in the soil or excreted fluid such as urine that seeps out from the superabsorbent polymer, thus releasing the oxidative decomposition accelerator inside them, and causing the oxidative decomposition accelerator to be spread out across the entire absorbent article, with the mobile medium being moisture in the soil or excreted fluid such as urine that has seeped out from the absorbent body, and therefore oxidative decomposition of each synthetic resin sheet by the oxidative decomposer can be even more efficiently and reliably accelerated by the oxidative decomposition accelerator.

The absorbent body of one or more embodiments may also be composed of a first layer situated on the skin side and comprising a plurality of the superabsorbent polymer particles, and a second layer adjacent to the non-skin side of the first layer and comprising a plurality of the water-sensitive capsules. If the absorbent body has such a construction, then even when excreted fluid such as urine discharged by the wearer during use of the absorbent article reaches the absorbent body, the excreted fluid will be absorbed by the superabsorbent polymer particles of the first layer situated on the skin side of the absorbent body, and will be even less likely to reach the oxidative decomposition accelerator in the water-sensitive capsules of the second layer that is adjacent to the non-skin side of the first layer (that is, the oxidative decomposition accelerator will be even less likely to reach the oxidative decomposer in each synthetic resin sheet with excreted fluid as the mobile medium), and therefore activation of the accelerating function of the oxidative decomposition accelerator during use of the absorbent article can be even more reliably inhibited.

Incidentally, while the aforementioned embodiments are not provided with an outer sheet situated on the non-skin side of the back sheet 3 or a leakproof sheet situated between the absorbent body 4 and the back sheet 3, there is no limitation to this aspect according to one or more embodiments, and the absorbent article may be provided with an outer sheet or leakproof sheet as in one or more embodiments.

An absorbent article to which one or more embodiments is applied is not limited to a tape-like disposable diaper as in the embodiments described above, and it may be applied to various types of absorbent articles such as pants-type disposable diapers, light incontinence pads, panty liners and sanitary napkins. Furthermore, the synthetic resin sheet composing the absorbent article may include any of various sheets in addition to the top sheet or back sheet, depending on the type of absorbent article in which it is to be applied. Examples of such sheets include liquid-permeable diffusion sheets which are disposed between the top sheet and absorbent body or between the absorbent body and back sheet, and which diffuse excreted fluid such as urine in the lengthwise direction or widthwise direction; and liquid-impermeable cover sheets disposed on the skin side of the top sheet of a pants-type disposable diaper or the like.

The absorbent article of one or more embodiments is not restricted to the embodiments described above and the examples described below, and can incorporate appropriate combinations, substitutes and modifications within a range that is not outside the scope of the present invention. Incidentally, the ordinal terms "first" and "second" as used throughout the present specification serve merely to distinguish between two of many embodiments and are not used to mean any relative ordering, precedence or importance.

EXAMPLES

One or more embodiments will now be explained in greater detail using examples and comparative examples, with the understanding that the embodiments are not limited only to these examples.

Example 1

(1) Production of Synthetic Resin Sheet

A polyethylene resin containing a commercially available oxidative decomposer ("P-Life", trade name of P-Life Japan, Inc., SMC2360) in the mixing ratio (mass %) listed in Table 3 below was kneaded in an extruder, and then an inflation method was used to produce a polyethylene film with a thickness of 25 μm.

(2) Oxidative Decomposition Acceleration Treatment With Oxidative Decomposition Accelerator After cutting the produced polyethylene film to a prescribed size (1 cm×6 cm), the polyethylene film was immersed in an aqueous solution containing sodium percarbonate as an oxidative decomposition accelerator in the mixing proportion listed in Table 3 (mass ratio (parts by mass) with respect to 100 parts by mass of the oxidative decomposer), and the aqueous solution was shaken for 7 days under temperature conditions of 37° C. for oxidative decomposition acceleration treatment, to obtain an oxidative decomposition acceleration-treated polyethylene film for Example 1. The oxidative decomposition acceleration treatment was carried out at a shaking speed of 120 rpm using a shaking apparatus (FLK-L180-E) by Font Labo Co. inside an incubator by As One Corp. (I-COVER incubating cover).

Examples 2 to 10

Oxidative decomposition acceleration-treated polyethylene films for Examples 2 to 10 were obtained in the same manner as Example 1, except that the oxidative decomposer mixing ratio, oxidative decomposition accelerator mixing proportion and type of oxidative decomposition accelerator were changed as shown in Table 3.

Comparative Example 1

A polyethylene film for Comparative Example 1 was produced in the same manner as Example 1, except that oxidative decomposition acceleration treatment with an oxidative decomposition accelerator was not carried out.

Comparative Example 2

A polyethylene film for Comparative Example 2 was produced in the same manner as Example 2, except that oxidative decomposition acceleration treatment with an oxidative decomposition accelerator was not carried out.

Comparative Example 3

An oxidative decomposition acceleration-treated polyethylene film for Comparative Example 3 was produced in the same manner as Example 1, except that the oxidative decomposition accelerator mixing proportion was changed as shown in Table 3.

The disintegration time ($D_h$) of each polyethylene film of Examples 1 to 10 and Comparative Examples 1 to 3 was measured according to <Method of measuring disintegration time ($D_h$) by heat acceleration test at 80° C.> above. In addition, the disintegration time before activation of the accelerating function by the oxidative decomposition accelerator was calculated as the "quality assurance period before disposal (years)", from the decomposition rate index ($D_i$) of the oxidative decomposer and the aforementioned approximation, and based on this disintegration time ($D_h$), a measure of 1 day (24 hours) of disintegration time corresponding to 4 months in an environment at 24° C. was utilized to calculate the disintegration time after activation of the accelerating function by the oxidative decomposition accelerator, as the "decomposition period after disposal (years)". The results for the composition of each polyethylene film and the measurement results for the disintegration time, as well as the calculated quality assurance period before disposal and decomposition period after disposal, are shown in Table 3.

TABLE 3

| | Oxidative decomposer (SMC2360) | | Oxidative decomposition accelerator | | Disintegration | Quality assurance | Decomposition |
|---|---|---|---|---|---|---|---|
| | Compositional ratio (mass %) | Decomposition rate index ($D_i$) (cm²/g) | Type | Content (pts by mass) | time $D_h$ (h) | period before disposal (years) | period after disposal (years) |
| Example 1 | 1.00 | 7.75 | Sodium percarbonate | 40 | 96 | 3.0 | 1.3 |
| Example 2 | 0.75 | 6.14 | Sodium percarbonate | 53 | 119 | 3.6 | 1.6 |
| Example 3 | 1.00 | 7.75 | Sodium percarbonate | 200 | 107 | 3.0 | 1.5 |
| Example 4 | 1.00 | 7.75 | Sodium percarbonate | 500 | 91 | 3.0 | 1.3 |
| Example 5 | 1.00 | 7.75 | Hydrogen peroxide | 40 | 21 | 3.0 | 0.3 |
| Example 6 | 1.00 | 7.75 | Hydrogen peroxide | 60 | 21 | 3.0 | 0.3 |
| Example 7 | 1.00 | 7.75 | Hydrogen peroxide | 80 | 21 | 3.0 | 0.3 |
| Example 8 | 0.75 | 6.14 | Hydrogen peroxide | 53 | 38 | 3.6 | 0.5 |
| Example 9 | 0.50 | 4.94 | Hydrogen peroxide | 80 | 43 | 4.0 | 0.6 |
| Example 10 | 0.25 | 3.00 | Hydrogen peroxide | 160 | 36 | 4.6 | 0.5 |
| Comp. Ex. 1 | 1.00 | 7.75 | — | — | 218 | 3.0 | — |
| Comp. Ex. 2 | 0.75 | 6.14 | — | — | 257 | 3.6 | — |
| Comp. Ex. 3 | 1.00 | 7.75 | Sodium percarbonate | 20 | 164 | 3.0 | 2.3 |

As shown in Table 3, the oxidative decomposition acceleration-treated polyethylene films of Examples 1 to 10 can notably shorten the polyethylene film (synthetic resin sheet) disintegration time, compared to the non-oxidative decomposition acceleration-treated polyethylene films of Comparative Examples 1 and 2. Most notably, Examples 5 to 10 which used hydrogen peroxide as the oxidative decomposition accelerator, had especially shortened disintegration times for the polyethylene films (synthetic resin sheets), regardless of the mixing proportion.

Based on comparison between Example 1 and Comparative Example 3, the disintegration time for a polyethylene film (synthetic resin sheet) can be drastically shortened when the mass ratio of the oxidative decomposition accelerator is 40 parts by mass or greater with respect to 100 parts by mass of the oxidative decomposer.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

1 Disposable diaper
2 Top sheet
3 Back sheet
4 Absorbent body
5 Side sheet
6 Stretching member
7 Connecting tape
8 Outer sheet
9 Leakproof sheet
$A_1, A_2$ Adhesive
$C_P$ Water-sensitive capsules

What is claimed is:

1. An absorbent article, comprising:
a top sheet that is liquid-permeable;
a back sheet that is liquid-impermeable; and
an absorbent body situated between the top sheet and the back sheet in a thickness direction of the absorbent article,
wherein at least one of the top sheet and the back sheet comprises a synthetic resin sheet that includes a synthetic resin component and an oxidative decomposer,
wherein the oxidative decomposer comprises a mixture of a carboxylate and a rare earth compound,
wherein the synthetic resin sheet includes the oxidative decomposer in a mass ratio such that a decomposition rate index (Di) is 7.8 or less, as determined by the following formula (1):

$$D_i = B_r \times S_a \quad (1)$$

where $B_r$ represents a mass ratio (g/g) of the oxidative decomposer with respect to the synthetic resin component, and $S_a$ represents a specific surface area (cm²/g) of the synthetic resin sheet,
wherein the absorbent article includes an oxidative decomposition accelerator in a mass ratio of 40 parts by mass or greater with respect to 100 parts by mass of the oxidative decomposer,
wherein the oxidative decomposition accelerator is a peroxide, and
wherein the oxidative decomposition accelerator is one or more of:
situated further toward a back sheet side in the thickness direction than the absorbent body, and
contained within water-sensitive capsules that are situated within the absorbent body.

2. The absorbent article according to claim 1, wherein the peroxide is sodium percarbonate or hydrogen peroxide.

3. The absorbent article according to claim 1, wherein the mass ratio of the oxidative decomposer in the synthetic resin sheet is such that the decomposition rate index (Di) is 3.0 or greater.

4. The absorbent article according to claim 1,
wherein the oxidative decomposition accelerator is situated on the same side of the absorbent body as the back sheet, and
wherein the back sheet is situated between the oxidative decomposition accelerator and the absorbent body.

5. The absorbent article according to claim 4, wherein the back sheet is non-air permeable.

6. The absorbent article according to claim 1,
wherein the oxidative decomposition accelerator is situated on the same side of the absorbent body as the back sheet, and
wherein the oxidative decomposition accelerator is situated between the absorbent body and the back sheet.

7. The absorbent article according to claim 1,
wherein the oxidative decomposition accelerator is contained within water-sensitive capsules and the absorbent body includes superabsorbent polymer particles and the water-sensitive capsules, and
wherein the water-sensitive capsules are in contact with the superabsorbent polymer particles.

8. The absorbent article according to claim 7,
wherein the absorbent body comprises a first layer and a second layer,
wherein the first layer is situated on a top sheet side in the thickness direction and comprises a plurality of the superabsorbent polymer particles, and
wherein the second layer is adjacent to the back side of the first layer and comprises a plurality of the water-sensitive capsules.

9. The absorbent article according to claim 2, wherein the mass ratio of the oxidative decomposer in the synthetic resin sheet is such that the decomposition rate index (Di) is 3.0 or greater.

10. The absorbent article according to claim 2,
wherein the oxidative decomposition accelerator is situated on the same side of the absorbent body as the back sheet, and
wherein the back sheet is situated between the oxidative decomposition accelerator and the absorbent body.

11. The absorbent article according to claim 10, wherein the back sheet is non-air permeable.

12. The absorbent article according to claim 3,
wherein the oxidative decomposition accelerator is situated on the same side of the absorbent body as the back sheet, and
wherein the back sheet is situated between the oxidative decomposition accelerator and the absorbent body.

13. The absorbent article according to claim 12, wherein the back sheet is non-air permeable.

14. The absorbent article according to claim 2,
wherein the oxidative decomposition accelerator is situated on the same side of the absorbent body as the back sheet, and
wherein the oxidative decomposition accelerator is situated between the absorbent body and the back sheet.

15. The absorbent article according to claim 3,
wherein the oxidative decomposition accelerator is situated on the same side of the absorbent body as the back sheet, and
wherein the oxidative decomposition accelerator is situated between the absorbent body and the back sheet.

16. The absorbent article according to claim 4,
wherein the oxidative decomposition accelerator is situated on the same side of the absorbent body as the back sheet, and
wherein the oxidative decomposition accelerator is situated between the absorbent body and the back sheet.

17. The absorbent article according to claim 5,
wherein the oxidative decomposition accelerator is situated on the same side of the absorbent body as the back sheet, and
wherein the oxidative decomposition accelerator is situated between the absorbent body and the back sheet.

18. The absorbent article according to claim 2,
wherein the oxidative decomposition accelerator is contained within water-sensitive capsules and the absorbent body includes superabsorbent polymer particles and the water-sensitive capsules, and
wherein the water-sensitive capsules are in contact with the superabsorbent polymer particles.

19. The absorbent article according to claim 3,
wherein the oxidative decomposition accelerator is contained within water-sensitive capsules and the absorbent body includes superabsorbent polymer particles and the water-sensitive capsules, and
wherein the water-sensitive capsules are in contact with the superabsorbent polymer particles.

20. The absorbent article according to claim 4,
wherein the oxidative decomposition accelerator is contained within water-sensitive capsules and the absorbent body includes superabsorbent polymer particles and the water-sensitive capsules, and
wherein the water-sensitive capsules are in contact with the superabsorbent polymer particles.

* * * * *